(12) United States Patent
Ding et al.

(10) Patent No.: US 10,563,141 B2
(45) Date of Patent: Feb. 18, 2020

(54) CONVERSION OF CRUDE OIL TO PETROCHEMICALS

(71) Applicant: Saudi Arabian Oil Company, Dhahran (SA)

(72) Inventors: Lianhui Ding, Dhahran (SA); Essam Al-Sayed, Al-Khobar (SA); Duhaiman U. Al-Yami, Rabwah (SA); Abdennour Bourane, Ras Tanura (SA); Alberto Lozano Ballesteros, Dhahran (SA); Ibrahim Abba, Dhahran (SA)

(73) Assignee: Saudi Arabian Oil Company, Dhahran (SA)

(*) Notice: Subject to any disclaimer, the term of this patent is extended or adjusted under 35 U.S.C. 154(b) by 0 days.

(21) Appl. No.: 15/588,024

(22) Filed: May 5, 2017

(65) Prior Publication Data
US 2017/0327754 A1 Nov. 16, 2017

Related U.S. Application Data

(60) Provisional application No. 62/336,055, filed on May 13, 2016.

(51) Int. Cl.
*C10G 69/06* (2006.01)
*C10G 69/00* (2006.01)

(52) U.S. Cl.
CPC ....... *C10G 69/06* (2013.01); *C10G 2300/202* (2013.01); *C10G 2300/205* (2013.01); *C10G 2400/20* (2013.01); *C10G 2400/22* (2013.01); *C10G 2400/30* (2013.01)

(58) Field of Classification Search
CPC .......... C10G 69/06; C10G 69/02; C10G 9/00; C10G 15/00
See application file for complete search history.

(56) References Cited

U.S. PATENT DOCUMENTS

| | | | |
|---|---|---|---|
| 3,755,143 A | 8/1973 | Hosoi et al. |
| 3,856,659 A | 12/1974 | Owen |
| 4,134,824 A | 1/1979 | Kamm et al. |
| 4,264,435 A | 4/1981 | Read et al. |
| 4,527,003 A | 7/1985 | Okamoto et al. |
| 4,587,011 A | 5/1986 | Okamoto et al. |
| 4,655,904 A | 4/1987 | Okamoto et al. |
| 4,725,349 A | 2/1988 | Okamoto et al. |
| 4,830,728 A | 5/1989 | Herbst et al. |
| 4,992,160 A | 2/1991 | Long et al. |

(Continued)

FOREIGN PATENT DOCUMENTS

| | | | |
|---|---|---|---|
| WO | 2013112967 | 8/2013 | |
| WO | 2015128040 A1 | 9/2015 | |
| WO | WO-2015128040 A1 * | 9/2015 | ........... C10B 57/045 |

OTHER PUBLICATIONS

Barker et al. (Kirk-Othmer Encyclopedia of Chemical Technology, 2005 (Year: 2005).*

(Continued)

*Primary Examiner* — Youngsul Jeong
(74) *Attorney, Agent, or Firm* — Dinsmore & Shohl LLP

(57) ABSTRACT

Embodiments for an integrated hydrotreating and steam pyrolysis process for the processing of crude oil comprising recycling the higher boiling point fraction of the upgraded crude oil to increase the yield of petrochemicals such as olefins and aromatics.

19 Claims, 4 Drawing Sheets

(56) References Cited

U.S. PATENT DOCUMENTS

| | | |
|---|---|---|
| 5,904,837 A | 5/1999 | Fujiyama et al. |
| 5,951,850 A | 9/1999 | Ino et al. |
| 6,033,555 A | 3/2000 | Chen et al. |
| 6,210,562 B1 | 4/2001 | Xie et al. |
| 6,656,346 B2 | 12/2003 | Ino et al. |
| 6,743,961 B2 | 6/2004 | Powers |
| 6,979,757 B2 | 12/2005 | Powers |
| 7,019,187 B2 | 3/2006 | Powers |
| 7,374,664 B2 | 5/2008 | Powers |
| 7,396,449 B2 | 7/2008 | Powers |
| 7,404,889 B1 | 7/2008 | Powers |
| 7,419,584 B2 | 9/2008 | Stell et al. |
| 7,550,642 B2 | 6/2009 | Powers |
| 7,744,747 B2 | 6/2010 | Halsey |
| 7,790,018 B2 | 9/2010 | Khan |
| 7,858,834 B2 | 12/2010 | Powers |
| 7,972,498 B2 | 7/2011 | Buchanan et al. |
| 9,096,806 B2 | 8/2015 | Abba et al. |
| 2006/0254956 A1 | 11/2006 | Khan |
| 2007/0090018 A1* | 4/2007 | Keusenkothen ....... C10G 9/007 208/106 |
| 2008/0277314 A1 | 11/2008 | Halsey |
| 2008/0283445 A1 | 11/2008 | Powers |
| 2009/0050523 A1 | 2/2009 | Halsey |
| 2013/0197285 A1 | 8/2013 | Shafi et al. |
| 2013/0248418 A1 | 9/2013 | Sayed et al. |
| 2014/0110308 A1 | 4/2014 | Bourane et al. |

OTHER PUBLICATIONS

International Search Report and Written Opinion pertaining to PCT/US2017/031670 dated Jul. 21, 2017.

* cited by examiner

CONVERSION OF CRUDE OIL TO PETROCHEMICALS

CROSS REFERENCE TO RELATED APPLICATIONS

This application claims the benefit of U.S. Provisional Application Ser. No. 62/336,055 filed May 13, 2016, incorporated herein by reference.

TECHNICAL FIELD

The present disclosure relates to an integrated hydrotreating and steam pyrolysis process for the processing of crude oil with the recycle of the heavy fraction of the upgraded crude oil to increase the yield of petrochemicals such as olefins and aromatics.

BACKGROUND

The lower olefins (for example, ethylene, propylene, butylene, butadiene and $C_4$ derivatives) and aromatics (for example, benzene, toluene and the xylenes) are basic and essential intermediates which are widely used in the petrochemical and chemical industries. Thermal cracking, or steam pyrolysis, is a major type of process for forming these materials, typically in the presence of steam and in the absence of oxygen. Feedstocks for pyrolysis can include petroleum gases and distillates such as naphtha, kerosene, and gas oil. However, the availability of these feedstocks is usually limited and requires costly and energy-intensive process steps in a crude oil refinery.

Studies have been conducted using heavy hydrocarbons as a feedstock for steam pyrolysis reactors. A major drawback in conventional heavy hydrocarbon steam pyrolysis operations is coke formation.

In addition, the yields and distributions of olefins and aromatics using heavy hydrocarbons as a feedstock for a steam pyrolysis reactor are different than those using light hydrocarbon feedstocks. Heavy hydrocarbons have a greater content of aromatics and a higher boiling point than light hydrocarbons. Greater aromaticity may be indicated by a greater Bureau of Mines Correlation Index (BMCI). BMCI is a measurement of aromaticity of a feedstock and is calculated as follows:

$$\text{BMCI}=87552/\text{VAPB}+473.5*(\text{sp. gr.})-456.8 \quad (1)$$

where:
VAPB=Volume Average Boiling Point in degrees Rankine and
sp. gr.=specific gravity of the feedstock.

As the BMCI decreases, ethylene yields are expected to increase. Therefore, highly paraffinic or low aromatic feeds are usually used for steam pyrolysis to obtain greater yields of desired olefins and to avoid greater yields of undesirable products and coke formation in the reactor coil section. In light of this boiling point differential, the specification may also utilize higher boiling point fraction when referring to heavy hydrocarbons and lower boiling point fraction when referring to light hydrocarbons.

To be able to respond to the growing demand of these petrochemicals, other type of feeds which can be made available in larger quantities, such as crude oil, are attractive to producers. "Crude oil" is to be understood to include whole crude oil from conventional sources, as well as crude oil that has undergone some pre-treatment. The term "crude oil" is also to be understood to include crude oil that has been subjected to water-oil separation, gas-oil separation, desalting, stabilization, or combinations of such. Using crude oil feeds will minimize or eliminate the likelihood of the refinery being a bottleneck in the production of these petrochemicals. Current integrated crude conditioning steam cracking processes fail to efficiently convert the heavy fraction of the upgraded crude oil into petrochemicals, such as olefins and aromatics, and result in high levels of coke formation.

SUMMARY OF THE INVENTION

Accordingly, there is a continual need for improved processes for converting crude oil which achieve increased yield of petrochemicals such as olefins and aromatics and decreased levels of coke formation.

Embodiments of the present disclosure meet those needs by providing integrated hydrotreating and steam pyrolysis processes for the direct processing of crude oil with the recycle of the heavy fraction of the upgraded crude oil to increase the yield of petrochemicals such as olefins and aromatics.

In accordance with one embodiment, a process for upgrading crude oil is provided. The process comprises mixing a crude oil stream with a hydrogen stream to yield a crude oil and hydrogen mixture and passing the crude oil and hydrogen to a to a hydroprocessing reactor operating at a temperature from 300 to 450° Celsius (C) and a pressure from 30 to 200 bars. The hydroprocessing reactor comprises hydroprocessing catalysts. The hydroprocessing catalysts can serve to hydrodesulfurize, hydrodemetallize, hydrodenitrogenate (or combinations of such) the crude oil and hydrogen mixture to produce a hydrotreated mixture. The process further comprises passing the hydrotreated mixture to a separator unit to separate the hydrotreated mixture into a lower boiling point fraction and a higher boiling point fraction. The higher boiling point fraction has a greater concentration of aromatics and a greater boiling point than the lower fraction, and the higher boiling point fraction has a boiling point of at least 500° C. The process further comprises thermally cracking the lower boiling point fraction in a steam cracking furnace operating at a coil outlet temperature from 700 to 900° C. to yield a cracking effluent comprising olefins and aromatics, and recycling the higher boiling point fraction for mixing with the crude oil and hydrogen mixture upstream of the hydroprocessing reactor to facilitate further upgrading of the crude oil.

Additional features and advantages of the embodiments will be set forth in the detailed description which follows, and in part will be readily apparent to those skilled in the art or recognized by practicing the embodiments described in the instant application, including the detailed description which follows, the claims, as well as the appended drawings.

Figure 1:
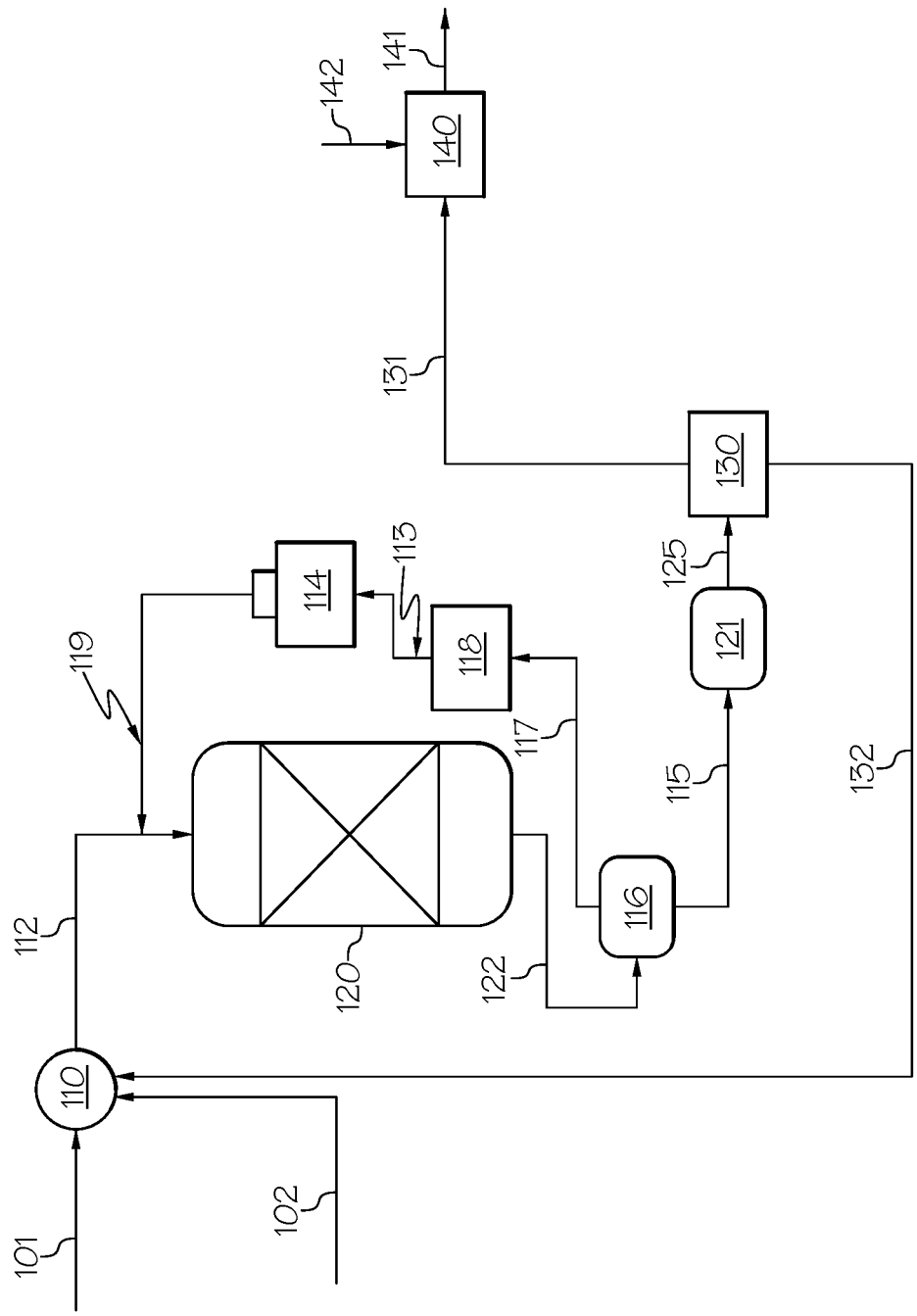
FIG. 1 is a process flow diagram of an embodiment of an integrated hydroprocessing and steam pyrolysis process with the recycle of the higher boiling point fraction of the upgraded crude oil.

The embodiments set forth in the drawings are illustrative in nature and not intended to be limiting to the claims. Moreover, individual features of the drawings will be more fully apparent and understood in view of the detailed description.

DETAILED DESCRIPTION OF THE INVENTION

Embodiments of the present disclosure are directed to integrated hydrotreating and steam pyrolysis processes for the direct processing of crude oil with the recycle of the higher boiling point fraction of the upgraded crude oil to increase the yield of petrochemicals such as olefins and aromatics.

Figure 2:
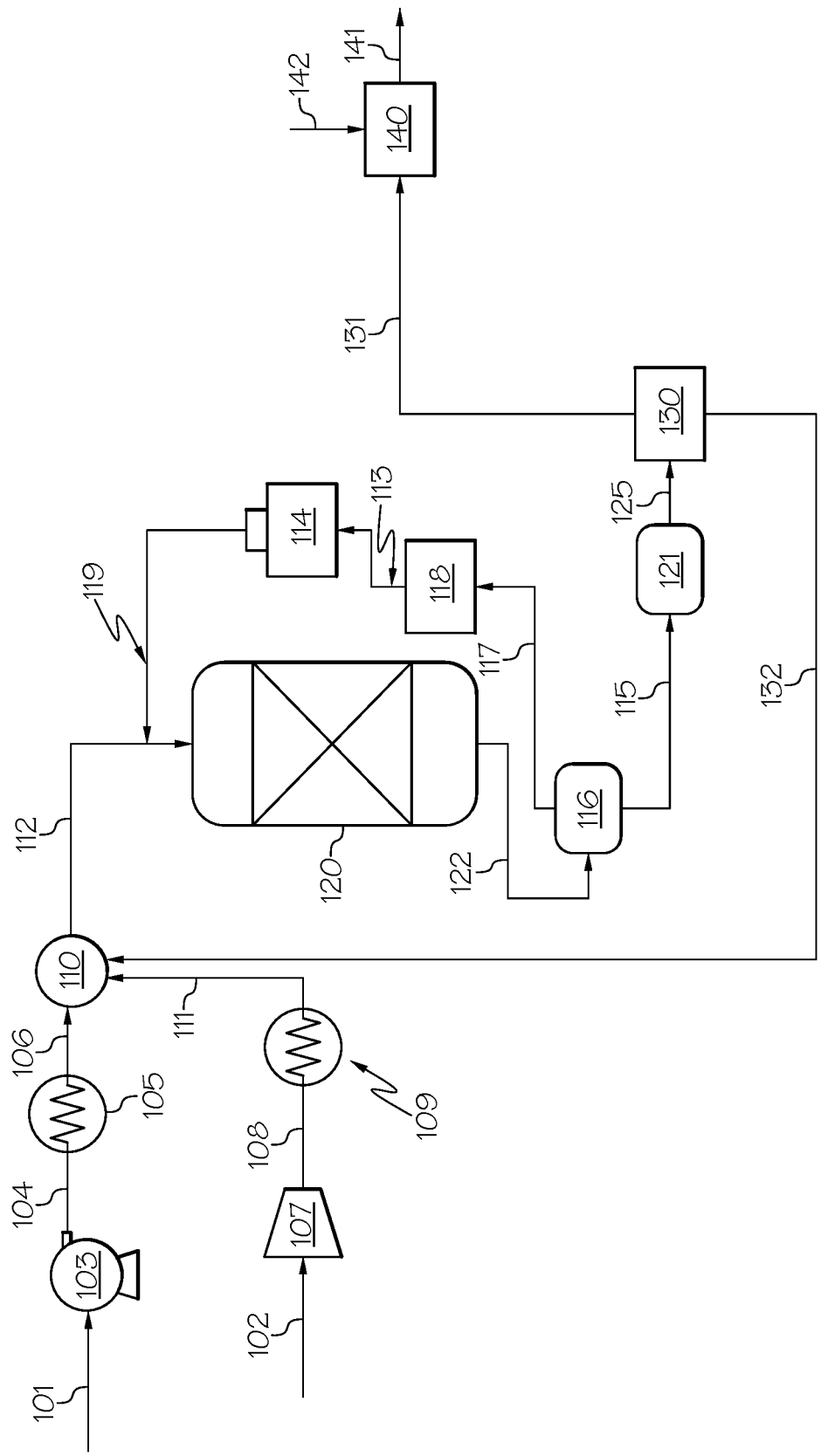
FIG. 2 is a process flow diagram of an additional embodiment of an integrated hydroprocessing and steam pyrolysis process with the recycle of the higher boiling point fraction of the upgraded crude oil.
Figure 3:
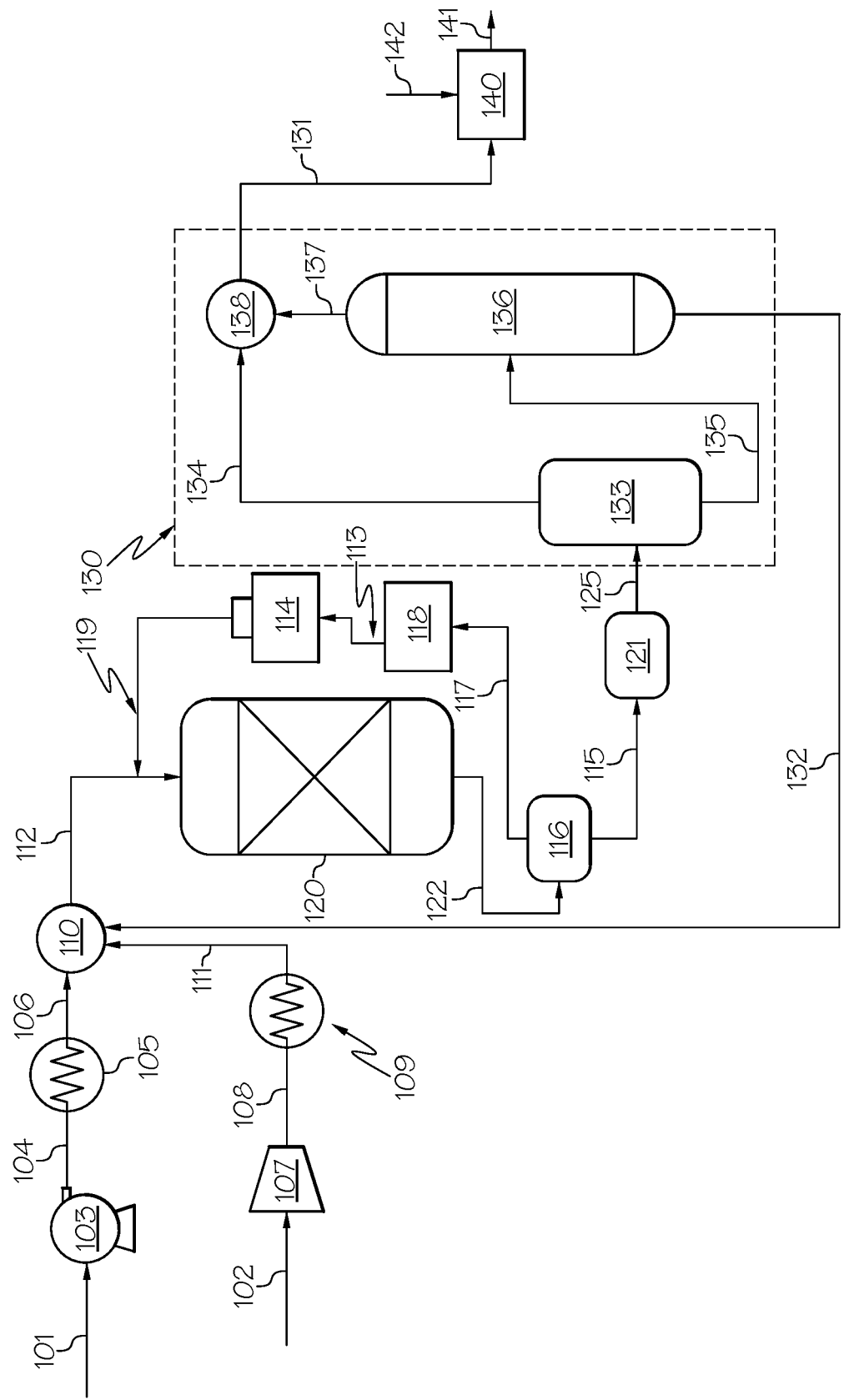
FIG. 3 is a process flow diagram of another embodiment of an integrated hydroprocessing and steam pyrolysis process with the recycle of the higher boiling point fraction of the upgraded crude oil.
Figure 4:
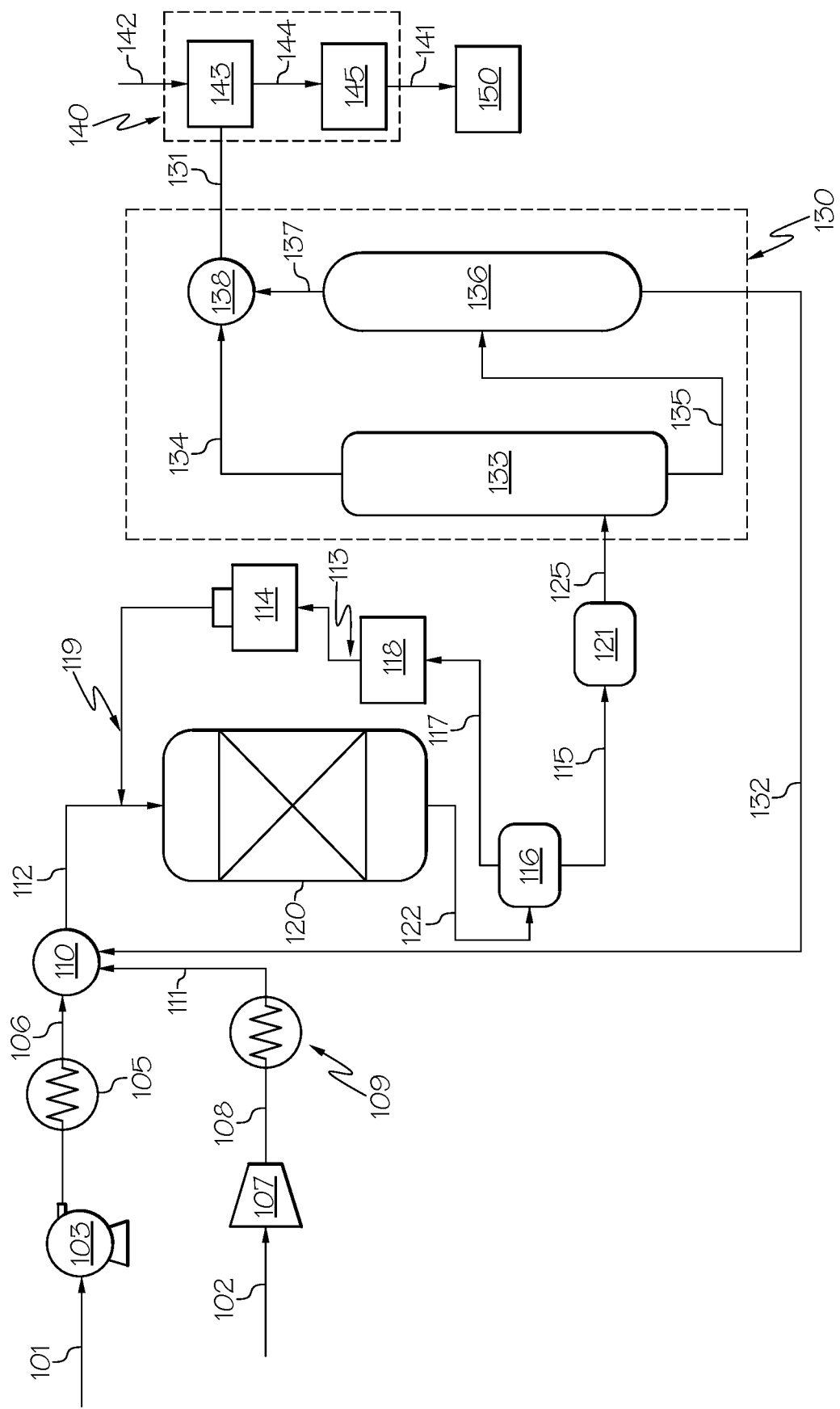
FIG. 4 is a process flow diagram of a further embodiment of an integrated hydroprocessing and steam pyrolysis process with the recycle of the higher boiling point fraction of the upgraded crude oil.

A process flow diagram including an integrated hydroprocessing and steam pyrolysis process with the recycle of the higher boiling point fraction of the upgraded crude oil is shown in FIGS. 1 to 4. In some embodiments, the process for upgrading crude oil comprises mixing a crude oil stream 101 with a hydrogen stream 102 to yield a crude oil and hydrogen mixture 112. As previously described, "crude oil" is to be understood to include whole crude oil from conventional sources, as well as crude oil that has undergone some pre-treatment. In some embodiments, "crude oil" can include crude oil from unconventional sources such as fracking light oil and other natural gas condensates. The term "crude oil" is also to be understood to include crude oil that has been subjected to water-oil separation, gas-oil separation, desalting, stabilization, or combinations of such. In certain embodiments of the process, the crude oil stream 101 has an API Gravity (°) of 25° to 50°. For example and as depicted in FIGS. 2 to 4, the crude oil stream 101 can first be optionally passed through a pump 103 to create a pressurized crude oil stream 104 before being mixed with the hydrogen stream 102. Thus, in certain embodiments, the process includes pressurizing the crude oil stream 101. In some embodiments, the crude oil stream 101 or pressurized crude oil stream 104 can be passed through a heater 105 to create a preheated crude oil stream or preheated and pressurized crude oil steam 106, respectively. Thus, in certain embodiments the process includes preheating the crude oil stream 101 to a temperature of at least 300° C. prior to mixing with the hydrogen stream 102. In some embodiments, the hydrogen stream 102 can be imported hydrogen, recycled hydrogen from downstream units, or a combination of such. Downstream units that can provide recycled hydrogen 119 for the hydrogen steam 120 include, for example, the optional high pressure cold or hot separator 116, the steam cracking furnace 140, and combinations of such. In certain embodiments, the process of upgrading crude oil that includes the use of recycled hydrogen can further comprise a minimum purge of the recycled hydrogen in order to avoid a buildup of contaminants in the recycle loop. Additionally, the hydrogen stream can be optionally passed through a compressor 107 to create a pressurized hydrogen stream 108 before being mixed with the crude oil stream 101, the pressurized crude oil stream 104, or the preheated and pressurized crude oil steam 106. Furthermore, the hydrogen stream can be optionally passed through a heater 109 to create a preheated hydrogen stream or a preheated and pressurized hydrogen stream 111, before being mixed with the crude oil stream 101, the pressurized crude oil stream 104, or the preheated and pressurized crude oil steam 106. In some embodiments, the heater serves to heat the hydrogen stream (or pressurized hydrogen stream) to a temperature of at least 300° C.

In some embodiments, the process for upgrading crude oil further comprises passing the crude oil and hydrogen mixture 112 to a hydroprocessing reactor 120. The hydroprocessing reactor 120 includes an inlet for receiving the crude oil and hydrogen mixture 112, and an outlet for discharging a hydrotreated mixture 122. In certain embodiments, the hydroprocessing reactor 120 operates under parameters effective to hydrodemetallize, hydrodearomatize, hydrodenitrogenate, hydrodesulfurize, hydrocrack, or combinations of such the crude oil and hydrogen mixture 112, thus producing the hydrotreated mixture 122. For example, in some embodiments, the hydroprocessing reactor 120 can operate at a temperature from 300 to 450° C. Further temperature ranges include from 300 to 330° C., from 300 to 350° C., from 320 to 360° C., from 340 to 380° C., from 360 to 400° C., from 380 to 420° C., from 400 to 430° C., and from 420 to 450° C. In some embodiments, the hydroprocessing reactor 120 can operate at a pressure from 30 to 200 bars. Further pressure ranges include from 30 to 60 bars, from 30 to 100 bars, from 50 to 100 bars, 75 to 125 bars, 100 to 150 bars, 125 to 175 bars, and 150 to 200 bars. In some embodiments, the liquid hourly space velocity (LHSV) of the hydroprocessing reactor 120 is from 0.1 to 2.0 h$^{-1}$. Further ranges for the LHSV include from 0.1 to 0.5 h$^{-1}$, from 0.5 to 1.0 h$^{-1}$, from 1.0 to 1.5 h$^{-1}$, and from 1.5 to 2.0 h$^{-1}$.

In certain embodiments, the hydroprocessing reactor 120 can include one or more unit operations as are known to those of skill in the art. For example, the hydroprocessing reactor 120 can include a plurality of reaction vessels, each containing an effective amount of one or more catalysts, such as hydrodemetallization catalyst, and hydroprocessing catalysts having hydrodearomatization, hydrodenitrogenation, hydrodesulfurization, hydrocracking functions, or combinations of such. Alternatively, the hydroprocessing reactor 120 can include one or more separation zones, each containing an effective amount of hydrodemetallization catalyst, and an effective amount of hydroprocessing catalysts having hydrodearomatization, hydrodenitrogenation, hydrodesulfurization, hydrocracking functions, or combinations of such. Alternatively, the hydroprocessing reactor 120 can include one or more catalyst layers containing an effective amount of hydrodemetallization catalyst, and one or more catalyst layers containing an effective amount of hydroprocessing catalyst having hydrodearomatization, hydrodenitrogenation, hydrodesulfurization, hydrocracking functions, or combinations of such. In some embodiments, the hydroprocessing reactor 120 can include one or more hydrogen quenches, as are known to those of skill in the art. The one or more hydrogen quenches are used to control the reaction temperature in the hydroprocessing reactor, and are achieved by introducing a hydrogen stream between the one or more reaction vessels, one or more separation zones, or one or more catalyst layers of the hydroprocessing reactor 120. The hydrogen stream used for the hydrogen quenches can be imported hydrogen, recycled hydrogen from downstream units, or a combination of such. Downstream units that can provide recycled hydrogen for the hydrogen quenches include, for example, the optional high pressure cold or hot separator or steam, the steam cracking furnace 140, and combinations of such.

In some embodiments, the hydroprocessing reactor 120 includes a plurality of catalyst layers. As depicted in FIGS.

2 to 4, the hydroprocessing reactor 120 can include two or more catalyst layers, 123 and 124. In further embodiments, the hydroprocessing reactor 120 includes a plurality of reaction vessels each containing one or more catalyst layers, for example, of different function. In certain embodiments, the hydroprocessing reactor 120 can include hydroprocessing catalysts which demetallize and desulfurize the crude oil and hydrogen mixture to produce a hydrotreated mixture 122. In some embodiments, the hydroprocessing catalysts include at least one metal from Periodic Table Groups 8 to 10, at least metal from Group 6, or combinations of at least one metal from Groups 8 to 10 and at least one metal from Group 6. In other embodiments, the hydroprocessing catalysts include cobalt (Co) and nickel (Ni). In further embodiments, the hydroprocessing catalysts include molybdenum (Mo) and tungsten (W) supported on a support material. In certain embodiments, the support material includes alumina.

In some embodiments, the hydroprocessing reactor 120 includes a hydrodemetallization catalyst. In other embodiments, the hydrodemetallization catalyst can be included in a separate reaction vessel (not shown), or in a separation zone. For example, in certain embodiments, the hydrodemetallization catalyst is included in a separate catalyst layer from other catalyst layers. In other embodiments, the hydrodemetallization catalyst can be included in a separate reaction vessel (not shown), or in a separate separation zone. In certain embodiments, the hydrodemetallization catalyst can be supported on a support material. In some embodiments, the support material includes alumina. In certain embodiments, the hydrodemetallization catalyst can based on a gamma alumina support material, with a surface area of from 140 to 240 meters$^2$/gram (m$^2$/g). Further surface area ranges include from 140 to 160 m$^2$/g, from 160 to 180 m$^2$/g, from 180 to 200 m$^2$/g, from 200 to 220 m$^2$/g, and from 220 to 240 m$^2$/g. This catalyst has a very high pore volume, for example, in excess of 1 centimeters$^3$/gram (cm$^3$/g). The pore size itself is typically predominantly macroporous, which are pores that are larger than 75 micrometers (μm). This is to provide a large capacity for the uptake of metals on the catalysts surface and optionally dopants. The active metals on the catalyst surface are sulfides of Ni and Mo in the ratio Ni/Ni+Mo<0.15. The concentration of Ni is lesser on the hydrodemetallization catalyst than other catalysts, as some Ni and vanadium (V) is anticipated to be deposited from the feedstock itself during the removal, acting as catalyst. The dopant used can be one or more of phosphorus (P), boron (B), silicon (Si), and halogens. In certain embodiments, the catalyst can be in the form of alumina extrudates or alumina beads. In other embodiments, alumina beads are used to facilitate un-loading of the catalyst hydrodemetallization layer in the reactor as the metals uptake will range between from 30 to 100% at the top of the layer.

In certain embodiments, the hydroprocessing reactor 120 includes an intermediate catalyst. The intermediate catalyst can also be used to perform a transition between the hydrodemetallization and the hydrodesulfurization function. In some embodiments, the intermediate catalyst can be included in a separate reaction vessel (not shown), or in a separation zone. In some embodiments, the intermediate catalyst is included with the hydrodemetallization catalyst. For example, the intermediate catalyst can be included in the hydrometallization catalyst layer. In some embodiments, the intermediate catalyst is included with the hydrodesulfurization catalyst. For example, the intermediate catalyst can be included in the hydrodesulfurization catalyst layer. In certain embodiments, the intermediate catalyst is included in a separate catalyst layer. For example, the hydrodemetallization catalyst, the intermediate catalyst, and the hydrodesulfurization catalyst are included in separate catalyst layers. In some embodiments, the intermediate catalyst can be supported on a support material. The support material can include alumina. The intermediate catalyst can include intermediate metal loadings and pore size distribution. The catalyst can include alumina based support in the form of extrudates, optionally at least one catalytic metal from Group 6 (for example, Mo, W, or combinations of such), or at least one catalytic metals from Groups 8 to 10 (for example, Ni, Co, or combinations of such), or combinations of such. The intermediate catalyst can also contain optionally at least one dopant selected from B, P, Si, and halogens. Physical properties include a surface area of from 140 to 200 m$^2$/g. Further surface area ranges include from 140 to 160 m$^2$/g, from 160 to 180 m$^2$/g, or from 180 to 200 m$^2$/g. Physical properties also include a pore volume of at least 0.6 cm$^3$/g. Physical properties further include pores which are mesoporous and in the range of from 12 to 50 nanometers (nm). Additional ranges include from 12 to 20 nm, from 20 to 30 nm, from 30 to 40 nm, or from 40 to 50 nm.

In some embodiments, the hydroprocessing reactor 120 includes a hydrodesulfurization catalyst. In some embodiments, the hydrodesulfurization catalyst can be included in a separate reaction vessel (not shown), or in a separation zone. For example, the hydrodesulfurization catalyst can be included in a separate catalyst layer from other catalyst layers. In certain embodiments, the hydrodemetallization catalyst, the intermediate catalyst, and the hydrodesulfurization catalyst are included in separate catalyst layers. In certain embodiments, the hydrodemetallization catalyst can be supported on a support material. In some embodiments, the support material includes alumina. In some embodiments, the hydrodesulfurization catalyst can include those having alumina based support materials with a surface area towards the upper end of the hydrodemetallization range, for example, ranging from 180 to 240 m$^2$/g. Additional ranges include from 180 to 195 m$^2$/g, from 195 to 210 m$^2$/g, from 210 to 225 m$^2$/g, or from 225 to 240 m$^2$/g. This required greater surface for hydrodesulfurization results in relatively smaller pore volume, for example, less than 1 cm$^3$/g. The hydrodesulfurization catalyst contains at least one element from Group 6, such as Mo and at least one element from Groups 8 to 10, such as Ni. The catalyst also comprises at least one dopant selected from B, P, Si and halogens. In certain embodiments, cobalt is used to provide relatively increased levels of desulfurization. The metals loading for the active phase is increased as the required activity is greater, such that the molar ratio of Ni/Ni+Mo is in the range of from 0.1 to 0.3 and the (Co+Ni)/Mo molar ratio is in the range of from 0.25 to 0.85.

In certain embodiments, the hydroprocessing reactor 120 can include a final catalyst designed to perform hydrogenation of the feedstock (rather than a primary function of hydrodesulfurization), for example as described in Appl. Catal. A General, 204 (2000) 251. In other embodiments, the final catalyst can be included in a separate reaction vessel (not shown), or in a separation zone. For example, the final catalyst can be included in a separate catalyst layer from other catalyst layers. In certain embodiments, the final catalyst can be supported on a support material. In certain embodiments, the support material can include alumina. The final catalyst may be promoted by Ni. Physical properties include a surface area towards the greater end of the range, for example, from 180 to 240 m$^2$/g. Additional ranges include from 180 to 195 m$^2$/g, from 195 to 210 m$^2$/g, from 210 to 225 m²/g, and from 225 to 240 m²/g. This required increased surface to perform hydrogenation results in relatively smaller pore volume, for example, less than 1 cm³/g.

Referring to FIGS. 1 to 4, the process for upgrading crude oil optionally further comprises cooling the hydrotreated mixture 122 from the hydroprocessing reactor 120 in a heat exchanger (not shown) and passing the hydrotreated mixture 122 to a high pressure cold or hot separator 116. The high pressure cold or hot separator 116 serves to separate gas and liquid products of the hydrotreated mixture 122. Separator tops 117 are cleaned in an amine unit 118 and a resulting hydrogen rich gas stream 113 that is optionally passed to a recycling compressor 114 to be used as a recycled gas 119 in the hydroprocessing reactor 120. A bottoms stream 115 from the high pressure separator 116, which is in a substantially liquid phase, is cooled and introduced to a low pressure cold separator 121 in which it is separated into a gas stream and a liquid stream 125. Gases from low pressure cold separator 121 include hydrogen, $H_2S$, $NH_3$ and any light hydrocarbons, such as C1-C4 hydrocarbons. These gases may be optionally passed for further processing, such as flare processing or fuel gas processing.

Referring to FIGS. 1 to 4, the process for upgrading crude oil further comprises passing the liquid stream 125 from the low pressure separator 121 to a separator unit 130. The separator unit 130 functions to separate the lower boiling point fraction 131 from the higher boiling point fraction 132 of the hydrotreated mixture 122. In some embodiments, the higher boiling point fraction 132 has a boiling point of at least 500° C. In some embodiments, the lower boiling point fraction 131 has a boiling point of less than 500° C. In other embodiments, the lower boiling point fraction 131 has a boiling point range of less than 500° C. to less than 560° C., while the higher boiling point fraction 132 has a boiling point range of greater than 500° C. to greater than 560° C. Characteristics and compositions of the lower boiling point fraction 131 include a light naphtha fraction, a heavy naphtha fraction, a kerosene fraction, a diesel fraction, and a gas oil fraction boiling between 370° C. and 540° C. Characteristics and compositions of the higher boiling point fraction 132 include a vacuum residue fraction boiling above 540° C. Thus, the lower boiling point fraction 131 includes a greater concentration of "<$C_{40}$ hydrocarbons" (hydrocarbons with less than 40 carbon atoms) than the higher boiling point fraction 132, while the higher boiling point fraction 132 has a greater concentration of ">C40" hydrocarbons (hydrocarbons with greater than 40 carbon atoms) than the lower boiling point fraction 131. Additionally, the higher boiling point fraction 132 includes a greater concentration of aromatics than the lower boiling point fraction 131. The separator unit 130 includes an inlet for receiving the hydrotreated mixture 122, an outlet for discharging the lower boiling point fraction 131, and an outlet for discharging the higher boiling point fraction 132.

Various components are contemplated for the separation unit 130. In certain embodiments, the separation unit 130 comprises a flash vessel 133 and a distillation vessel 136 downstream of the flash vessel 133, as depicted in FIGS. 3 and 4. In some embodiments, the separation unit 130 can include one or more flash vessels 133. In certain embodiments, the flash vessel 133 is a flash drum. In some embodiments of the process for upgrading crude oil, separation by the separator unit 130 comprises separating the hydrotreated mixture 122 in the flash vessel 133 into a first lower boiling point fraction 134 and a first higher boiling point fraction 135, where the first lower boiling point fraction 134 has a boiling point range less than 350° C., and the first higher boiling point fraction 135 has a boiling range greater than 350° C. Characteristics and compositions of the first lower boiling point fraction 134 include a light naphtha fraction, a heavy naphtha fraction, a kerosene fraction, and a diesel fraction. Characteristics and compositions of the first higher boiling point fraction 135 include a gas oil fraction boiling between 370° C. and 540° C. and a vacuum residue fraction boiling above 540° C. Thus, the first lower boiling point fraction 134 includes a greater concentration of "<$C_{18}$" hydrocarbons (hydrocarbons with less than 18 carbon atoms) than the first higher boiling point fraction 135, while the first higher boiling point fraction 135 has a greater concentration of ">$C_{18}$" hydrocarbons (hydrocarbons with less than 18 carbon atoms) than the first lower boiling point fraction 134. The flash vessel 133 can include an inlet for receiving the hydrotreated mixture 122 and an outlet for discharging the first lower boiling point fraction 134 and an outlet for discharging the first higher boiling point fraction 135. In certain embodiments, the hydrotreated mixture 122 is flashed in the flash vessel 133 at atmospheric pressure and at an inlet temperature between 350° C. and 450° C. Additional inlet temperature ranges include from 350 to 370° C., from 370 to 390° C., from 390 to 410° C., from 410 to 430° C., and from 430 to 450° C.

Referring to FIGS. 3 and 4, in certain embodiments, the process for upgrading crude oil further comprises passing the first higher boiling point fraction 135 to a distillation vessel 136. In some embodiments, the separation unit 130 can include one or more distillation vessels 136. In certain embodiments, the distillation vessel 136 can be a distillation tower, such as a vacuum distillation tower. Therefore, some embodiments of the process for upgrading crude oil further comprise separating the first higher boiling point fraction 135 in a distillation vessel 136 to yield a second lower boiling point fraction 137 and the higher boiling point fraction 132, where the second lower boiling point fraction 137 has a boiling point range of greater than 350° C. to less than 500° C., and the higher boiling point fraction 132 has a boiling point greater than 500° C. In other embodiments, the second lower boiling point fraction 137 has a boiling point range of greater than 350° C. to less than 500° C. to less than 560° C., and the higher boiling point fraction 132 has a boiling point range greater than 500° C. to greater than 560° C. Characteristics and compositions of the second lower boiling point fraction 137 include a gas oil fraction boiling between 370° C. and 540° C. As previously described, the characteristics and compositions of the higher boiling point fraction 132 include a vacuum residue fraction boiling above 540° C. Thus, the second lower boiling point fraction 137 includes a greater concentration of $C_{18}$-$C_{40}$ hydrocarbons than the higher boiling point fraction 132, while the higher boiling point fraction 132 has a greater concentration of ">$C_{40}$" hydrocarbons than the second lower boiling point fraction 137. The distillation vessel 136 can include an inlet for receiving the first higher boiling point fraction 135, an outlet for discharging the second lower boiling point fraction 137, and an outlet for discharging the higher boiling point fraction 132. In certain embodiments, the distillation tower operates at a temperature between 350° C. and 450° C. and at an absolute pressure of between 10 millimeters of mercury (mmHg) to 40 mmHg. Additional absolute pressure ranges include from 10 to 20 mmHg, from 20 to 30 mmHg, and from 30 to 40 mmHg.

Referring to FIGS. 1 to 4, in some embodiments, the process for upgrading crude oil further comprises passing the lower boiling point fraction 131 from the separator unit 130 to a steam cracking furnace 140. In embodiments in which the separation unit 130 comprises a flash vessel 133 and a distillation vessel 136 downstream of the flash vessel 133, the process for upgrading crude oil can further comprise combining the first lower boiling point fraction 134 from the flash vessel 133 and the second lower boiling point fraction 137 from the distillation vessel 136 in mixer 138 to yield the lower boiling point fraction 131. Therefore, in certain aspects, the process further includes thermally cracking the lower boiling point fraction 131 in the steam cracking furnace 140 in the presence of steam 142. The steam cracking furnace 140 operates under parameters effective to crack the lower boiling point fraction 131 into the desired products, including olefins (including ethylene, propylene, butenes, and butadiene), aromatics (including benzene, toluene, and xylenes), pyrolysis gasoline, pyrolysis gasoil, and pyrolysis oil. In certain embodiments, the steam cracking furnace 140 operates at a temperature from 700 to 900° C. to yield a cracking effluent 141 comprising olefins and aromatics. Further possible temperature ranges include from 700 to 750° C., from 750 to 800° C., from 800 to 850° C., or from 850 to 900° C.

Referring to FIG. 4, in some embodiments, the steam cracking furnace 140 comprises a convection section 143 and a pyrolysis section 145 downstream of the convection section 143. The convection section 143 and the pyrolysis section 145 can operate based on steam pyrolysis unit operations familiar to skilled person, that is, passing the lower boiling point fraction 131 to the convection section 143 in the presence of steam 142. The lower boiling point fraction 131, which serves as the pyrolysis feed stream, is first passed to an inlet of the convection section 143 in the presence of an effective amount of steam, such as through a steam inlet. An "effective amount of steam" is an amount of steam that serves as a diluent to keep the hydrocarbon molecules of the lower boiling point fraction 131 separated. In the convection section 143, the lower boiling point fraction 131 and steam 142 mixture is heated to a predetermined temperature, for example, using one or more waste heat streams or other suitable heating arrangement. In certain embodiments, the convection section 143 operates at a temperature from 700 to 900° C. Further temperature ranges may include from 700 to 750° C., from 750 to 800° C., from 800 to 850° C., or from 850 to 900° C. The heated mixture of the lower boiling point fraction 131 and additional steam 142 from the convention section 143 forms a post-convection light fraction 144.

Still referring to FIG. 4, in some embodiments, the post-convection light section 144 is passed from the convention section 143 to the pyrolysis section 145. The pyrolysis section 145 operates under parameters effective to crack the post-convection light section 144 into the cracking effluent 141. The cracking effluent 141 includes the desired products, including olefins (including ethylene, propylene, butenes, and butadiene), aromatics (including benzene, toluene, and xylenes), and pyrolysis gasoline.

In certain embodiments, steam cracking in the convection section 143 and pyrolysis section 145 is carried out using a temperature in the range of from 700° C. to 900° C. in the convection section 143 and in the pyrolysis section 145, a steam 142-to-light fraction 131 ratio in the convection section 143 in the range of from 0.3:1 to 2.0:1, and a residence time in the convection section 143 and in the pyrolysis section 145 in the range of from 0.05 seconds to 2 seconds.

Referring to FIGS. 1 to 4, in some embodiments, the process for upgrading crude oil further comprises recycling the higher boiling point fraction 132 from the separator unit 130 for mixing with the crude oil stream 101 (or alternatively the pressurized crude oil stream 104 or the preheated and pressurized crude oil steam 106) and hydrogen stream 102 (or alternatively the pressurized hydrogen stream 108) upstream of the hydroprocessing reactor 120 to facilitate further upgrading of the crude oil. In certain embodiments, the higher boiling point fraction 132 is recycled to the mixer 110 for mixing with the crude oil stream 101 (or alternatively the pressurized crude oil stream 104 or the preheated and pressurized crude oil steam 106) and hydrogen stream 102 (or alternatively the pressurized hydrogen stream 108). Unexpectedly, the recycling of the higher boiling point fraction 132 of unconverted oil from the separator unit 130 (and alternatively from the distillation vessel 136) for further upgrading of the crude oil results in improved yield of olefins (including ethylene, propylene, butenes, and butadiene) and aromatics (including benzene, toluene, and xylenes) in the steam cracking furnace 140 versus a process that does not include such recycling of the higher boiling point fraction 132. In certain embodiments, the process of upgrading crude oil that includes recycling of the higher boiling point fraction 132 results in improved yield of at least one of ethylene, propylene, butenes, and butadiene. In other embodiments, the process of upgrading crude oil that includes recycling of the higher boiling point fraction 132 results in improved yield of at least one of benzene, toluene, and xylenes. Additionally, such recycling of the higher boiling point fraction 132 of unconverted oil from the separator unit 130 (and alternatively from the distillation vessel 136) for further upgrading of the crude oil results in reduced coke formation in the steam cracking furnace 140 versus a process that does not include such recycling of the higher boiling point fraction 132. In certain embodiments, the process of upgrading crude oil that includes recycling of the higher boiling point fraction 132 can further comprise a minimum purge of the higher boiling point fraction 132 in order to avoid a buildup of contaminants in the recycle loop.

In some embodiments, the process for upgrading crude oil further comprises cooling the cracking effluent 141. In certain embodiments, the process comprises cooling the cracking effluent 141 to a temperature less than 200° C., for example, from between ambient temperature to 200° C. In some embodiments, the process for upgrading crude oil further comprises delivering the cracking effluent to additional separation units 150, such as coolers, gas-liquid separators, oil-gas separators, oil-liquid separators, fractionators, or combinations of such, as is known in the art. Additionally, in some embodiments the process for upgrading crude oil further comprises separating olefins from the cracking effluent 141 in a fractionator 150, as is known in the art.

For example, the cracking effluent 141 can be passed to an inlet of a quenching zone (not shown), with a quenching solution (for example, water, pyrolysis fuel oil, or combinations of such) introduced via a separate inlet to produce an intermediate quenched mixed product stream having a reduced temperature, for example, of 200° C. to 300° C., and spent quenching solution is discharged. The gas mixture effluent from the steam cracking furnace 140 is typically a mixture of hydrogen, methane, hydrocarbons, carbon dioxide and hydrogen sulfide. After cooling with water or oil quench, the mixture can be compressed in a multi-stage compressor zone, for example, in 4 to 6 stages, to produce a compressed gas mixture. The compressed gas mixture can be treated in a caustic treatment unit to produce a gas mixture depleted of hydrogen sulfide and carbon dioxide. The gas mixture can be further compressed in a compressor zone, and the resulting cracked gas typically undergoes a cryogenic treatment to be dehydrated, and is further dried by use of molecular sieves.

Furthermore, the cold cracked gas stream can be passed to a de-methanizer tower (not shown), from which an overhead stream is produced containing hydrogen and methane from the cracked gas stream. The bottoms stream from de-methanizer tower can then sent for further processing in a product separation zone, comprising fractionation towers including de-ethanizer, de-propanizer and de-butanizer towers. Process configurations with a different sequence of de-methanizer, de-ethanizer, de-propanizer and de-butanizer can also be employed.

After separation from methane at the de-methanizer tower and hydrogen recovery in hydrogen recovery unit, hydrogen having a purity of typically 80 to 95 percentage by volume (vol %) is obtained. Recovery methods in the hydrogen recovery unit include cryogenic recovery (for example, at a temperature of about −157° C.). The hydrogen stream can then be passed to a hydrogen purification unit, such as a pressure swing adsorption (PSA) unit to obtain a hydrogen stream having a purity of 99.9%+, or a membrane separation units to obtain a hydrogen stream with a purity of about 95%. The purified hydrogen stream can then be recycled back to serve as a major portion of the requisite hydrogen for the hydroprocessing zone. In addition, a minor proportion can be utilized for the hydrogenation reactions of acetylene, methylacetylene and propadienes. In addition, the methane stream from the hydrogen recovery unit can optionally be recycled to the steam cracker to be used as fuel for burners, heaters, or combinations of such.

Additionally, the bottoms stream from de-methanizer tower can be conveyed to an inlet of a product separation zone to be separated into methane, ethylene, propylene, butadiene, mixed butylenes and pyrolysis gasoline, which can be discharged via separate outlets. Pyrolysis gasoline generally includes $C_5$-$C_9$ hydrocarbons, and benzene, toluene and xylenes can be extracted from this cut.

The features of the present embodiments will be further illustrated in the Examples which follow.

EXAMPLES

Recycling of the higher boiling point fraction of the upgraded crude oil results in increased yield of aromatics and olefins:

A comparative study was conducted to evaluate the petrochemical yields from steam cracking the hydrotreated crude oil with the recycle of the higher boiling point fraction and without the recycle of the higher boiling point fraction according to the previously described processes, as shown in Table 1. SPYRO software (Technip Benelux B.V., located in Zoetermeer, Netherlands) was used to simulate the steam cracking process. The processing parameters for the SPYRO simulation included a temperature of 700° C. to 900° C., a steam to hydrocarbon ratio of 0.3:1 to 2.0:1, and a residence time of 0.05 seconds to 0.2 seconds. Table 1 lists additional conditions for the steam cracker.

As depicted in Table 1, recycling of the higher boiling point fraction of the upgraded crude oil results in increased yield of aromatics and olefins compared to the same process that does not include such recycling of the higher boiling point fraction.

TABLE 1

| Feed | Without recycle | 540° C. + recycled |
|---|---|---|
| based on steam cracker Conditions | | |
| HC-flow, grams/hour (g/h) | 3600 | 3600 |
| $H_2O$-flow, g/h | 3600 | 3600 |
| COT, ° C. | 840 | 840 |
| COP, absolute pressure (bar abs) | 1.8 | 1.8 |
| Yields, wt. % | | |
| Total Olefin | 40.3 | 45.6 |
| $H_2$ | 0.6 | 0.7 |
| $CH_4$ | 10.2 | 11.3 |
| $C_2H_6$ | 2.7 | 2.7 |
| $C_2H_4$ | 20.7 | 23.2 |
| $C_3H_8$ | 0.4 | 0.4 |
| $C_3H_6$ | 10.3 | 11.6 |
| n-$C_4H_{10}$ | 0.1 | 0.1 |
| i-$C_4H_{10}$ | 0.0 | 0 |
| Propadiene (PD) | 0.3 | 0.3 |
| $C_2H_2$ | 0.4 | 0.4 |
| t-2-$C_4H_8$ | 0.3 | 0.4 |
| 1-$C_4H_8$ | 1.1 | 1.1 |
| i-$C_4H_8$ | 1.2 | 1.4 |
| c-2-$C_4H_8$ | 0.3 | 0.3 |
| 1,3-$C_4H_6$ | 3.7 | 4.6 |
| Methylacetylene (MeAc) | 0.3 | 0.4 |
| $C_5$+ | 0.0 | |
| Benzene | 4.7 | 4.8 |
| Toluene | 3.8 | 4 |
| Xylenes | 1.2 | 1.1 |
| $C_5$-$C_{10}$ (excel. BTX) | 8.4 | 7.9 |
| $C_{10}$+ | 18.1 | 23 |
| Coke formation | | |
| Reactor (g coke/hour) | 0.6 | 0.8 |

It should not be understood the various aspects of the composite zeolite catalyst, the method of making the same, the method of making xylene using the same, and a system for making xylene using the same are described and such aspects may be utilized in conjunction with various other aspects.

In a first aspect, the disclosure provides a process for upgrading crude oil. The process comprises mixing a crude oil stream with a hydrogen stream to yield a crude oil and hydrogen mixture. Further, the process comprises passing the crude oil and hydrogen mixture to a hydroprocessing reactor operating at a temperature from 300 to 450° C. and a pressure from 30 to 200 bars. The hydroprocessing reactor comprises hydroprocessing catalysts which desulfurize and demetallize the crude oil and hydrogen mixture to produce a hydrotreated mixture. Additionally, the process includes passing the hydrotreated mixture to a separator unit to separate the hydrotreated mixture into a lower boiling point fraction and a higher boiling point fraction. The higher boiling fraction has a greater concentration of aromatics and a greater boiling point than the lower boiling point fraction. The higher boiling point fraction has a boiling point of at least 500° C. The process further comprises thermally cracking the lower boiling point fraction in a steam cracking furnace operating at a temperature from 700 to 900° C. to yield a cracking effluent comprising olefins and aromatics. Finally, the process includes recycling the higher boiling point fraction for mixing with the crude oil and hydrogen mixture upstream of the hydroprocessing reactor to facilitate further upgrading of the crude oil.

In a second aspect, the disclosure provides the process of the first aspect, in which the separation unit comprises a flash vessel and a distillation vessel downstream of the flash vessel.

In a third aspect, the disclosure provides the process of the first or second aspects, in which separation by the separator unit comprises a flash vessel which separates the hydrotreated mixture into a first lower boiling point fraction and a first higher boiling point fraction. The first lower boiling point fraction has a boiling point range of less than 350° C., and the first higher boiling point fraction has a boiling range of greater than 350° C. Separation by the separator unit also comprises a distillation vessel which separates the first higher boiling point fraction into a second lower boiling point fraction and the higher boiling point fraction. The second lower boiling point fraction has a boiling point range of greater than 350° C. to less than 500° C. and the higher boiling point fraction has a boiling point greater than 500° C.

In a fourth aspect, the disclosure provides the process of the third aspect, in which the process further comprises combining the first lower boiling point fraction and the second lower boiling point fraction to yield the lower boiling point fraction.

In a fifth aspect, the disclosure provides the process of any of the first through fourth aspects, in which the process further comprises preheating the crude oil to a temperature of at least 300° C. prior to mixing with the hydrogen stream.

In a sixth aspect, the disclosure provides the process of any of the first through fifth aspects, in which the hydroprocessing catalysts comprise at least one Group 8 metal, at least one Group 6 metal, or combinations thereof.

In a seventh aspect, the disclosure provides the process of the sixth aspect, in which the hydroprocessing catalysts comprise Co and Ni.

In an eighth aspect, the disclosure provides the process of any of the first through seventh aspects, in which the hydroprocessing catalysts comprise Mo and W supported on a support material.

In a ninth aspect, the disclosure provides the process of any of the first through eighth aspects, in which the support material comprises alumina.

In a tenth aspect, the disclosure provides the process of any of the first through ninth aspects in which the crude oil stream has an API Gravity (°) of 25° to 50°.

In an eleventh aspect, the disclosure provides the process of any of the first through tenth aspects, in which where the hydrogen stream comprises hydrogen and recycled hydrogen.

In a twelfth aspect, the disclosure provides the process of any of the first through eleventh aspects, in which the hydroprocessing reactor comprises a plurality of catalyst layers.

In a thirteenth aspect, the disclosure provides the process of any of the first through twelfth aspects, in which the liquid hourly space velocity (LHSV) of the hydroprocessing reactor is from 0.1 to 2.0 $h^{-1}$.

In a fourteenth aspect, the disclosure provides the process of any of the first through thirteenth aspects, in which the steam cracking furnace comprises a convection section and a pyrolysis section downstream of the convection section.

In a fifteenth aspect, the disclosure provides the process of the fourteenth aspect, in which the convection section has a steam to light fraction ratio of 0.3:1 to 2:0.1.

In a sixteenth aspect, the disclosure provides the process of the fourteenth or fifteenth aspects, in which the convection section allows for a reaction residence time of 0.05 to 2 seconds.

In a seventeenth aspect, the disclosure provides the process of any of the first through sixteenth aspects, in which the aromatics of the cracking effluent comprise one or more of benzene, toluene, and xylene.

In an eighteenth aspect, the disclosure provides the process of any of the first through seventeenth aspects, in which the process further comprises cooling the cracking effluent to a temperature less than 200° C.

In a nineteenth aspect, the disclosure provides the process of any of the first through eighteenth aspects, in which the process further comprises delivering the cracking effluent to gas-liquid separators, oil-liquid separators, or combinations thereof.

In a twentieth aspect, the disclosure provides the process of any of the first through nineteenth aspects, in which the process further comprises separating olefins from the cracking effluent in a fractionator.

It should be apparent to those skilled in the art that various modifications can be made to the described embodiments without departing from the spirit and scope of the claimed subject matter. Thus, it is intended that the specification cover the modifications and variations of the various described embodiments provided such modifications and variations are within the scope of the appended claims and their equivalents Throughout this disclosure ranges are provided. It is envisioned that each discrete value encompassed by the ranges are also included. Additionally, the ranges which may be formed by each discrete value encompassed by the explicitly disclosed ranges are equally envisioned.

What is claimed is:

1. A process for upgrading crude oil comprising:
mixing a crude oil stream with a hydrogen stream to yield a crude oil and hydrogen mixture;
passing the crude oil and hydrogen mixture to a hydroprocessing reactor operating at a temperature from 300 to 450° C. and a pressure from 30 to 200 bars, the hydroprocessing reactor comprising hydroprocessing catalysts which desulfurize and demetallize the crude oil and hydrogen mixture to produce a hydrotreated mixture;
passing the hydrotreated mixture to a separator unit to separate the hydrotreated mixture into a lower boiling point fraction and a higher boiling point fraction, where the higher boiling fraction has a greater concentration of aromatics and a greater boiling point than the lower boiling point fraction, and where the higher boiling point fraction has a boiling point of at least 500° C., where separation by the separator unit comprises:
a flash vessel which separates the hydrotreated mixture into a first lower boiling point fraction and a first higher boiling point fraction, where the first lower boiling point fraction has a boiling point range of less than 350° C. , and the first higher boiling point fraction has a boiling range of greater than 350° C.; and
a distillation vessel which separates the first higher boiling point fraction into a second lower boiling point fraction and the higher boiling point fraction, where the second lower boiling point fraction has a boiling point range of greater than 350° C. to less than 500° C. and the higher boiling point fraction has a boiling point range of greater than 500° C., where the lower boiling point fraction comprises the first lower boiling point fraction and/or the second lower boiling point fraction;
thermally cracking the lower boiling point fraction in a steam cracking furnace operating at a temperature from 700 to less than 850° C. to yield a cracking effluent comprising olefins and aromatics; and recycling the entirety of the higher boiling point fraction for mixing with the crude oil and hydrogen mixture upstream of the hydroprocessing reactor to facilitate further upgrading of the crude oil.

2. The process of claim 1, further comprising combining the first lower boiling point fraction and the second lower boiling point fraction to yield the lower boiling point fraction.

3. The process of claim 1, further comprising preheating the crude oil stream to a temperature of at least 300° C. prior to mixing with the hydrogen stream.

4. The process of claim 1, where the hydroprocessing catalysts comprise at least one Group VIII metal, at least one Group VI metal, or combinations thereof.

5. The process of claim 4, where the hydroprocessing catalysts comprise Co and Ni.

6. The process of claim 1, where the hydroprocessing catalysts comprise Mo and W supported on a support material.

7. The process of claim 6, where the support material comprises alumina.

8. The process of claim 1, where the crude oil stream has an API Gravity (°) of 25° to 50°.

9. The process of claim 1, where the hydrogen stream comprises a hydrogen and recycled hydrogen.

10. The process of claim 1, where the hydroprocessing reactor comprises a plurality of catalyst layers.

11. The process of claim 1, where a liquid hourly space velocity (LHSV) of the hydroprocessing reactor is from 0.1 to 2.0 $h^{-1}$.

12. The process of claim 1, where the steam cracking furnace comprises a convection section and a pyrolysis section downstream of the convection section.

13. The process of claim 12, where the convection section has a steam to light fraction ratio of 0.3:1 to 2:0.1, the light fraction representing a stream of the lower boiling point fraction.

14. The process of claim 12, where the convection section allows for a reaction residence time of 0.05 to 2 seconds.

15. The process of claim 1, where the aromatics of the cracking effluent comprise one or more of benzene, toluene, and xylene.

16. The process of claim 1, further comprising cooling the cracking effluent to a temperature less than 200° C.

17. The process of claim 1, further comprising delivering the cracking effluent to gas-liquid separators, oil-liquid separators, or combinations thereof.

18. The process of claim 1, further comprising separating olefins from the cracking effluent in a fractionator.

19. The process of claim 1, where thermally cracking the lower boiling point fraction is completed in the steam cracking furnace operating at a temperature from 700 to less than 800° C. to yield the cracking effluent comprising olefins and aromatics.

* * * * *